(12) United States Patent
Bottomy et al.

(10) Patent No.: US 10,077,995 B1
(45) Date of Patent: Sep. 18, 2018

(54) GAS DETECTION FLOW RATE CONTROLLER

(71) Applicants: Chris Bottomy, Panama City, FL (US); Marshall Black, Panama City, FL (US); Chris Smith, Panama City, FL (US)

(72) Inventors: Chris Bottomy, Panama City, FL (US); Marshall Black, Panama City, FL (US); Chris Smith, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/661,793

(22) Filed: Jul. 27, 2017

(51) Int. Cl.
*G01F 1/28* (2006.01)
*G01N 1/22* (2006.01)

(52) U.S. Cl.
CPC .............. *G01F 1/28* (2013.01); *G01N 1/2226* (2013.01); *G01N 2001/2238* (2013.01)

(58) Field of Classification Search
CPC ..... G01F 1/28; G01F 1/37; G01F 1/12; G01F 23/30; G01F 23/38; G01F 3/14; G01F 25/00
See application file for complete search history.

(56) References Cited

U.S. PATENT DOCUMENTS

| | | | | |
|---|---|---|---|---|
| 7,079,937 B2* | 7/2006 | Tanaka | ............... | F02D 41/18 701/102 |
| 7,082,827 B1* | 8/2006 | Samuelson | .......... | G01F 23/0023 73/308 |
| 7,322,231 B2* | 1/2008 | Trygg | ................. | G01F 1/24 73/250 |
| 7,463,991 B2* | 12/2008 | Shajii | ................. | G01F 25/0038 702/100 |
| 7,547,852 B2* | 6/2009 | Sallovitz | ............... | A01C 1/00 111/200 |
| 9,399,199 B2* | 7/2016 | Dille | ................... | G05D 7/0635 |
| 9,709,434 B1* | 7/2017 | Harper | ................ | G01F 23/66 |

* cited by examiner

*Primary Examiner* — Jewel V Dowtin
(74) *Attorney, Agent, or Firm* — James T. Shepherd

(57) ABSTRACT

A flow rate control apparatus includes an adjustable valve receiving a flow of a gas. A conduit has a first end coupled to the valve. The conduit includes a translucent or transparent portion thereof whose longitudinal axis is adapted to be aligned with a force of gravity with a visual scale being disposed on the translucent/transparent portion. The visual scale is indicative of gas flow rates moving through the conduit. A ball disposed in the translucent/transparent portion has an outer diameter that is less than an inner diameter of the translucent/transparent portion. A tube support, coupled to the second end of the conduit, is adapted to hold a gas detection tube wherein the gas flow flowing around the ball is introduced into the gas detection tube from the second end of the conduit.

14 Claims, 3 Drawing Sheets

GAS DETECTION FLOW RATE CONTROLLER

ORIGIN OF THE INVENTION

The invention described herein may be manufactured and used by or for the Government of the United States of America for Governmental purposes without payment of any.

FIELD OF THE INVENTION

The invention relates generally to gas flow controllers, and more particularly to a flow rate control apparatus for controlling the flow rate of a gas being supplied to a gas detection tube.

BACKGROUND OF THE INVENTION

The U.S. Navy currently uses high-pressure compressor assemblies to recharge Self-Contained Breathing Apparatus (SCBA) aboard its ships. The recharge of SCBAs requires Compressed Gas Association (CGA) grade "d" air which can only be supplied by a compressor that is approved to this standard as evidenced by quarterly air sample checks. Compressor air testing uses gas detection tubes to check air composition produced by the compressor that is ultimately to be used to sustain life in hazardous environments. Testing requirements include determining gas compositions for water vapor, oxygen, carbon dioxide, carbon monoxide, and hydrocarbons. These components are considered to be the gases necessary for metabolism, as well as the critical contaminants. Testing tubes for each gas type are mounted into an air test kit. Accuracy mandates that these tubes receive a set flow rate of gas for a predetermined test duration. Currently, the flow rate is determined by a flow restrictor inside the testing manifold. Unfortunately, flow restrictors can be inaccurate when it comes to flow rate thereby generating erroneous gas composition measurements. In addition, flow restrictors do not provide real-time feedback and/or adjustability with respect to a gas's flow rate.

SUMMARY OF THE INVENTION

Accordingly, it is an object of the present invention to provide a flow rate control apparatus.

Another object of the present invention is to provide a flow rate control apparatus that can provide feedback on the flow rate of a gas being supplied to a gas detection tube.

Still another object of the present invention is to provide a flow rate control apparatus for controlling the flow rate of a gas being supplied to a gas detection tube.

Other objects and advantages of the present invention will become more obvious hereinafter in the specification and drawings.

In accordance with the present invention, a flow rate control apparatus is provided for use with gas detection tubes. An adjustable valve having an input is adapted to receive a flow of a gas. The adjustable valve has an output for outputting a portion of the gas flow based on a flow control position of the adjustable valve. A conduit has a first end coupled to the output of the adjustable valve and has a second end. The conduit includes a translucent or transparent portion thereof whose longitudinal axis is adapted to be aligned with a force of gravity. A visual scale is disposed on the translucent/transparent portion of the conduit. The visual scale is indicative of gas flow rates moving through the conduit. A ball disposed in the translucent/transparent portion of the conduit has an outer diameter that is less than an inner diameter of the translucent/transparent portion of the conduit. A tube support, coupled to the second end of the conduit, is adapted to hold a gas detection tube wherein the gas flow flowing around the ball is introduced into the gas detection tube from the second end of the conduit.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
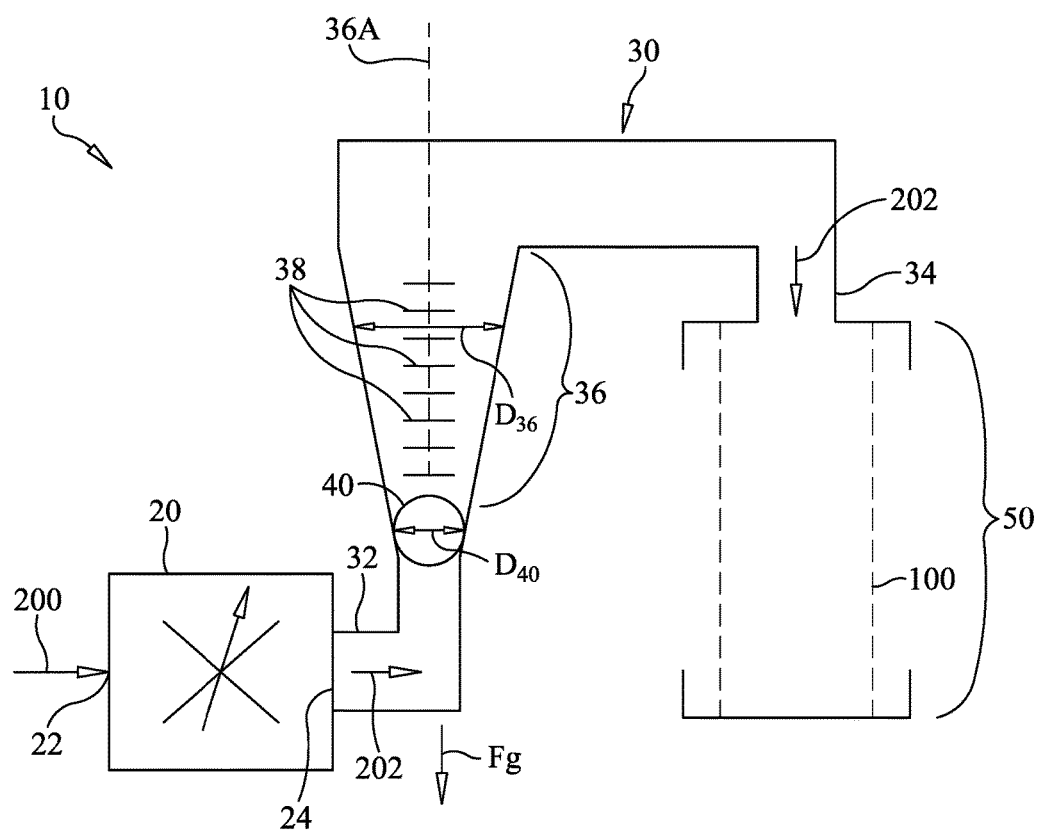
FIG. 1 is a schematic view of a flow rate control apparatus for controlling the flow rate of a gas being supplied to a gas detection tube in accordance with an embodiment of the present invention.

Referring now to the drawings and more particularly to FIG. 1, a flow rate control apparatus for controlling the flow rate of a gas being supplied to a gas detection tube in accordance with an embodiment of the present invention is shown and is referenced generally by numeral 10. The gas detection tube, illustrated by dashed lines 100, is not part of flow rate control apparatus 10. As is known in the art, gas detection tube 100 contains material (not shown) that reacts with a specified flow rate of a gas in order to produce a visual change in the material (e.g., color change) when a particular gas component is present in the gas in a specified quantity. Flow rate control apparatus 10 allows a user to provide and adjust the gas's specified flow rate as well as monitor the flow rate during the course of a test.

Flow rate control apparatus 10 includes an adjustable valve 20, a conduit 30, a ball/float 40 disposed in conduit 30, and a tube support 50 for holding gas detection tube 100. A flow of a gas to be tested (referenced by arrow 200) is supplied to an input 22 of adjustable valve 20 that is controllable by a user to adjust the flow rate of gas 202 discharged from the output 24 of valve 20. A variety of types of valves can be used for adjustable valve 20 without departing from the scope of the present invention.

Conduit 30 is coupled on one end 32 thereof to output 24 and on the other end 34 thereof to tube support 50. As will be explained further below, conduit 30 and ball/float 40 cooperate to provide a user with visual feedback regarding the flow rate of gas 202 discharged at output 24 that is to be supplied to gas detection tube 100. Conduit 30 includes a region 36 having a longitudinal axis 36A that is aligned with the force of gravity $F_g$. Region 36 is partially or completely translucent or transparent such that ball/float 40 is visible from the outside of region 36. Region 36 includes visual marking(s) 38 thereon that are indicative of flow rates of gas 202 moving through conduit 30.

Ball/float 40 has an outer diameter $D_{40}$ that is less than the inner diameter $D_{35}$ of region 36. Inner diameter $D_{35}$ increases along a direction that opposes the force of gravity $F_g$. The length of region 36 and amount of increase of inner diameter $D_{35}$ can be calibrated for a specific application. When there is no gas discharged into conduit 30, ball/float 40 should rest in the lowermost end of region 36. This can be accomplished with an inside diameter of conduit 30 just below region 36 that is less than diameter $D_{40}$, or can be accomplished by the provision of stops (not shown) disposed on the inside walls of conduit 30 just below region 36.

When flow 202 is discharged from valve 20 at its output 24, the flow of gas acts on ball/float 40 to move it upward in region 36. Valve 20 is adjusted to keep ball/float 40 aligned with specified ones of markings 38 indicative of a desired flow rate. The increasing inner diameter $D_{35}$ provides for increased flow rates as ball/float 40 is driven further against the force of gravity $F_g$. Ball/float 40 can be hollow or solid without departing from the scope of the present invention. By way of an illustrative example, ball/float 40 can be a solid ball made from an acetal homopolymer resin material such as the commercially-available DELRIN.

Tube support 50 can be any support structure that provides support for gas detection tube 100 during a gas test. Typically, tube support 50 holds gas detection tube 100 upright or in alignment with the force of gravity. Gas discharge end 34 of conduit 30 is coupled to tube support 50 such that the flow of gas 202 exiting discharge end 34 is emitted into gas detection tube 100. Seals (not shown) can be provided between tube support 50 and gas detection tube 100 in ways well known in the art. As is also known in the art, the flow of gas 202 exits tube 100 after passing through the test material (not shown) contained therein. Accordingly, tube support 50 is typically configured to allow the discharged gas to escape into the ambient environment.

Figure 2:
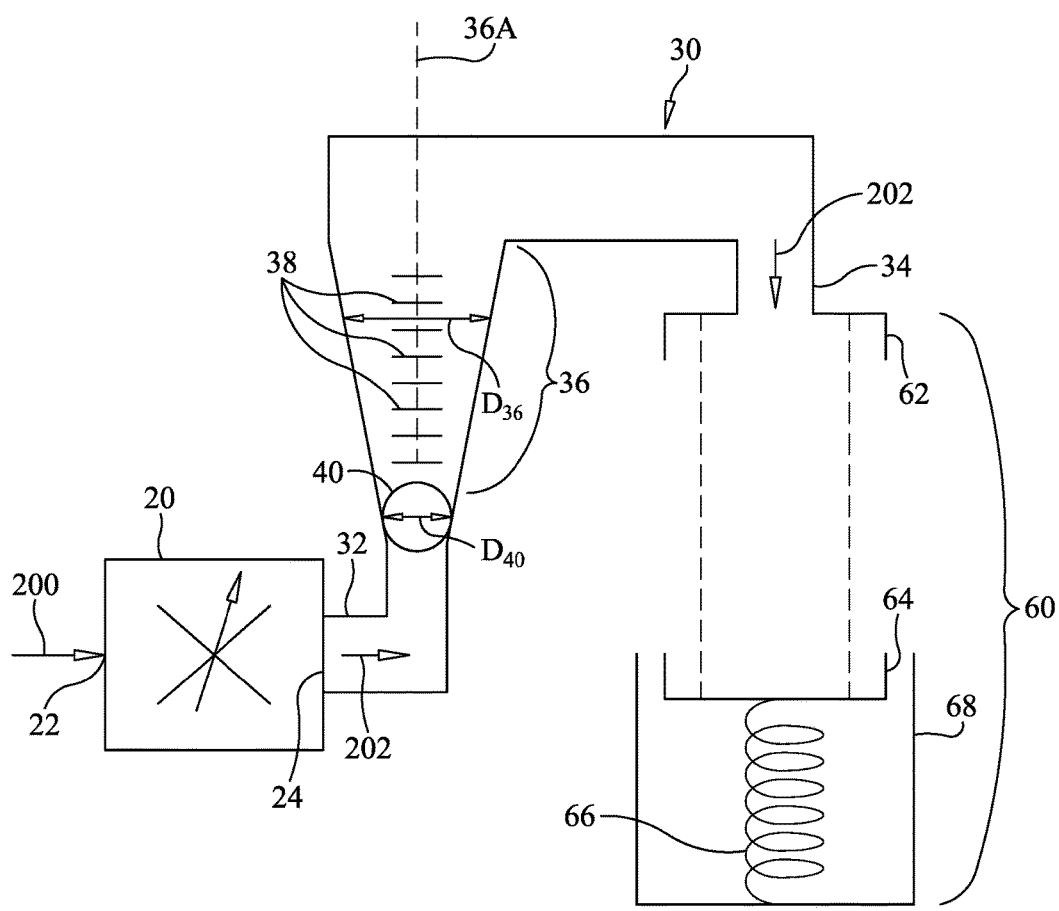
FIG. 2 is a schematic view of a flow rate controller apparatus in accordance with another embodiment of the present invention.

By way of an illustrative example, FIG. 2 illustrates another embodiment of the present invention in which a tube support 60 is configured to elastically retain gas detection tube 100. More specifically, tube support 60 includes a first tube support 62 coupled to discharge end 34 of conduit 30. A second tube support 64 is mounted on a spring 66 supported in a base container 68. As in the previous embodiment, seals (not shown) would typically be provided to form an airtight seal between gas detection tube 100 and tube support 60. Spring 66 and tube support 64 cooperate to keep gas detection tube 100 elastically biased towards tube support 62 to thereby retain tube 100 during test operations. Base container 68 can also serve as a catch basin for any gas detection material (not shown) falling out of gas detection tube 100.

Figure 3:
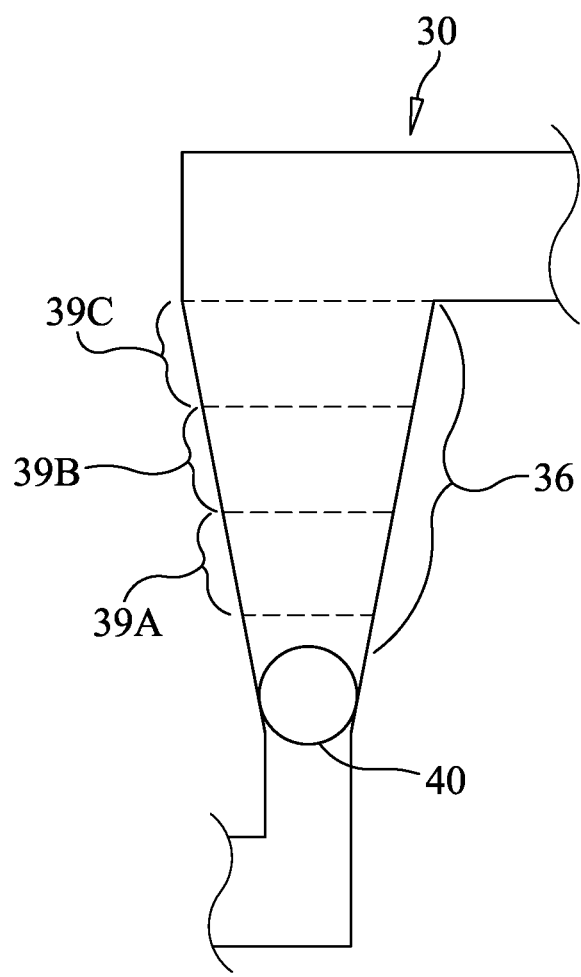
FIG. 3 is an isolated view of the portion of the conduit containing the floating ball with the conduit having a GOOD/BAD flow rate region scale indicator in accordance with another embodiment of the present invention.

The above-described markings 38 on region 36 can be actual flow rate values. However, the present invention is not so limited. For example, FIG. 3 illustrates an isolated view of another embodiment of region 36 on which flow rate markings are realized by colored regions 39A, 39B and 39C. By way of an illustrative example, regions 39A and 39C could be colored red to indicate a flow rate that is unacceptable or "BAD" (i.e., too low or too high), and region 39B could be colored green to indicate a flow rate that is acceptable or "GOOD".

The advantages of the present invention are numerous. The flow rate control apparatus allows a user to adjust a gas flow rate and easily monitor that flow rate. The apparatus has particular utility for testing gas supplied to gas detection tubes used in the evaluation of charging gas for SCBA tanks.

Although the invention has been described relative to specific embodiments thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A flow rate control apparatus for use with gas detection tubes, comprising:
   an adjustable valve having an input adapted to receive a flow of a gas, said adjustable valve having an output for outputting a portion of said flow based on a flow control position of said adjustable valve;
   a conduit having a first end coupled to said output of said adjustable valve and having a second end, said conduit including a portion thereof whose longitudinal axis is adapted to be aligned with a force of gravity, said portion of said conduit being one of translucent and transparent;
   a visual scale disposed on said portion of said conduit, said visual scale being indicative of flow rates of said portion of said flow moving through said conduit;
   a ball disposed in said portion of said conduit, wherein an outer diameter of said ball is less than an inner diameter of said portion of said conduit; and
   a tube support coupled to said second end of said conduit, said tube support adapted to hold a gas detection tube wherein said portion of said flow flows around said ball and is introduced into the gas detection tube from said second end of said conduit.

2. A flow rate control apparatus as in claim 1, wherein said tube support aligns the gas detection tube with the force of gravity.

3. A flow rate control apparatus as in claim 1, wherein said inner diameter of said portion of said conduit varies along a length thereof.

4. A flow rate control apparatus as in claim 1, wherein said ball comprises a solid ball of an acetal homopolymer resin material.

5. A flow rate control apparatus as in claim 1, wherein said tube support comprises:
   a first support coupled to said second end of said conduit; and
   a second support spaced apart from said first support, wherein said second support and said first report are spaced apart and configured to hold the gas detection tube in place therebetween.

6. A flow rate control apparatus as in claim 5, wherein said second support is elastically biased towards said first support.

7. A flow rate control apparatus for use with gas detection tubes, comprising:
   an adjustable valve having an input adapted to receive a flow of a gas, said adjustable valve having an output for outputting a portion of said flow based on a flow control position of said adjustable valve;
   a conduit having a first end coupled to said output of said adjustable valve and having a second end, said conduit including a portion thereof whose longitudinal axis is adapted to be aligned with a force of gravity and whose inner diameter increases along a direction opposing the force of gravity, said portion of said conduit being one of translucent and transparent;

a visual scale disposed on said portion of said conduit, said visual scale being indicative of flow rates of said portion of said flow moving through said conduit;

a ball disposed in said portion of said conduit, wherein an outer diameter of said ball is less than said inner diameter of said portion of said conduit; and a tube support coupled to said second end of said conduit, said tube support adapted to hold a gas detection tube wherein said portion of said flow flows around said ball and is introduced into the gas detection tube from said second end of said conduit.

8. A flow rate control apparatus as in claim 7, wherein said tube support aligns the gas detection tube with the force of gravity.

9. A flow rate control apparatus as in claim 7, wherein said ball comprises a solid ball of an acetal homopolymer resin material.

10. A flow rate control apparatus as in claim 7, wherein said tube support comprises:

a first support coupled to said second end of said conduit; and a second support spaced apart from said first support, wherein said second support and said first report are spaced apart and configured to hold the gas detection tube in place therebetween.

11. A flow rate control apparatus as in claim 10, wherein said second support is elastically biased towards said first support.

12. A flow rate control apparatus for use with gas detection tubes, comprising:

an adjustable valve having an input adapted to receive a flow of a gas, said adjustable valve having an output for outputting a portion of said flow based on a flow control position of said adjustable valve;

a conduit having a first end coupled to said output of said adjustable valve and having a second end, said conduit including a portion thereof whose longitudinal axis is adapted to be aligned with a force of gravity and whose inner diameter increases along a direction opposing the force of gravity, said portion of said conduit being one of translucent and transparent;

a visual scale disposed on said portion of said conduit, said visual scale being indicative of flow rates of said portion of said flow moving through said conduit;

a ball disposed in said portion of said conduit, wherein an outer diameter of said ball is less than said inner diameter of said portion of said conduit; and a tube support having a first support coupled to said second end of said conduit and having a second support spaced apart from said first support, wherein said second support and said first report are spaced apart and configured to hold the gas detection tube therebetween in alignment with the force of gravity, wherein said portion of said flow flows around said ball in said portion of said conduit and is introduced into the gas detection tube from said second end of said conduit.

13. A flow rate control apparatus as in claim 12, wherein said ball comprises a solid ball of an acetal homopolymer resin material.

14. A flow rate control apparatus as in claim 12, wherein said second support is elastically biased towards said first support.

\* \* \* \* \*